United States Patent [19]

Abdel-Rahman

[11] Patent Number: 5,108,264
[45] Date of Patent: Apr. 28, 1992

[54] METHOD AND APPARATUS FOR REAL TIME COMPENSATION OF FLUID COMPRESSIBILITY IN HIGH PRESSURE RECIPROCATING PUMPS

[75] Inventor: Mahmoud F. Abdel-Rahman, Westgrove, Pa.

[73] Assignee: Hewlett-Packard Company, Palo Alto, Calif.

[21] Appl. No.: 570,183

[22] Filed: Aug. 20, 1990

[51] Int. Cl.$^5$ ............................ F04B 1/26; F04B 49/00
[52] U.S. Cl. ........................................ 417/20; 417/22; 417/32
[58] Field of Search ................. 417/18, 32, 2, 19, 20, 417/22

[56] References Cited

U.S. PATENT DOCUMENTS

| | | | |
|---|---|---|---|
| 3,787,882 | 1/1974 | Fillmore et al. | 417/32 X |
| 4,352,636 | 10/1982 | Patterson et al. | 417/42 X |
| 4,681,513 | 7/1987 | Saito | 417/18 X |
| 4,797,207 | 1/1989 | Honganen et al. | 417/265 X |
| 4,808,077 | 2/1989 | Kan et al. | 417/45 X |
| 4,883,409 | 11/1989 | Stohmeier et al. | 417/43 |

*Primary Examiner*—Leonard E. Smith
*Attorney, Agent, or Firm*—Richard F. Schuette

[57] ABSTRACT

The invention is a method and apparatus for significantly improving the performance of a reciprocating pump by delivering the pumping fluid at a desired pressure and flow rate with minimal flow fluctuations. The compressibility of the pumping fluid directly effects volumetric flow rate and mass flow rate. The method includes the step of sensing various pump parameters related to said compressibility and adjusting the pumping speed to make appropriate accommodations. In particular, the compressibility of the pumping fluid is effected by the adiabatic heating of the pumping fluid during compression, variations in pumping fluid density, leaks in the check valves of cylinder/piston seals and the primary and secondary switching losses in the fluid flow occurring when the primary and secondary pistons reverse direction.

12 Claims, 18 Drawing Sheets

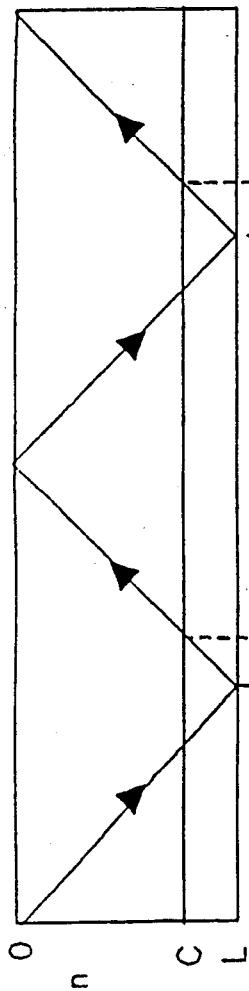
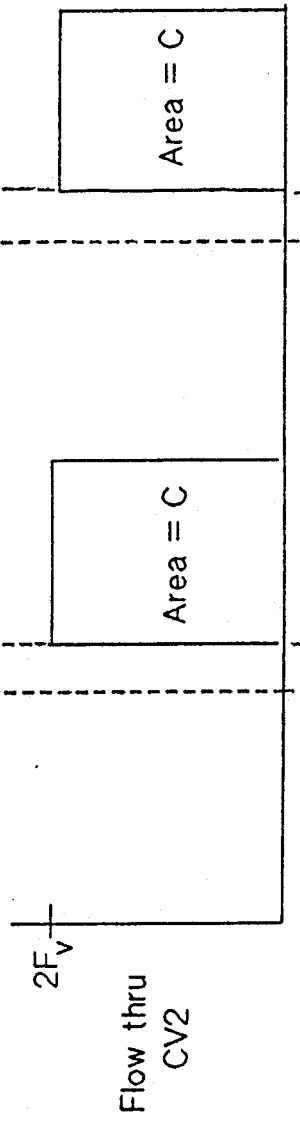
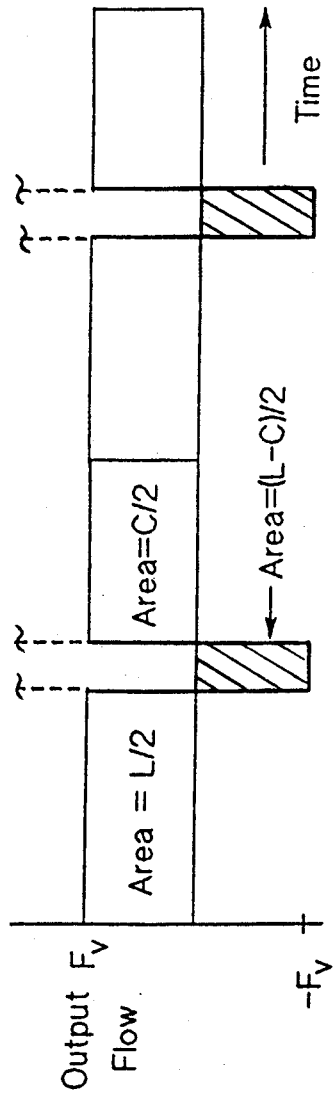
FIG 5A
FIG 5B
FIG 5C

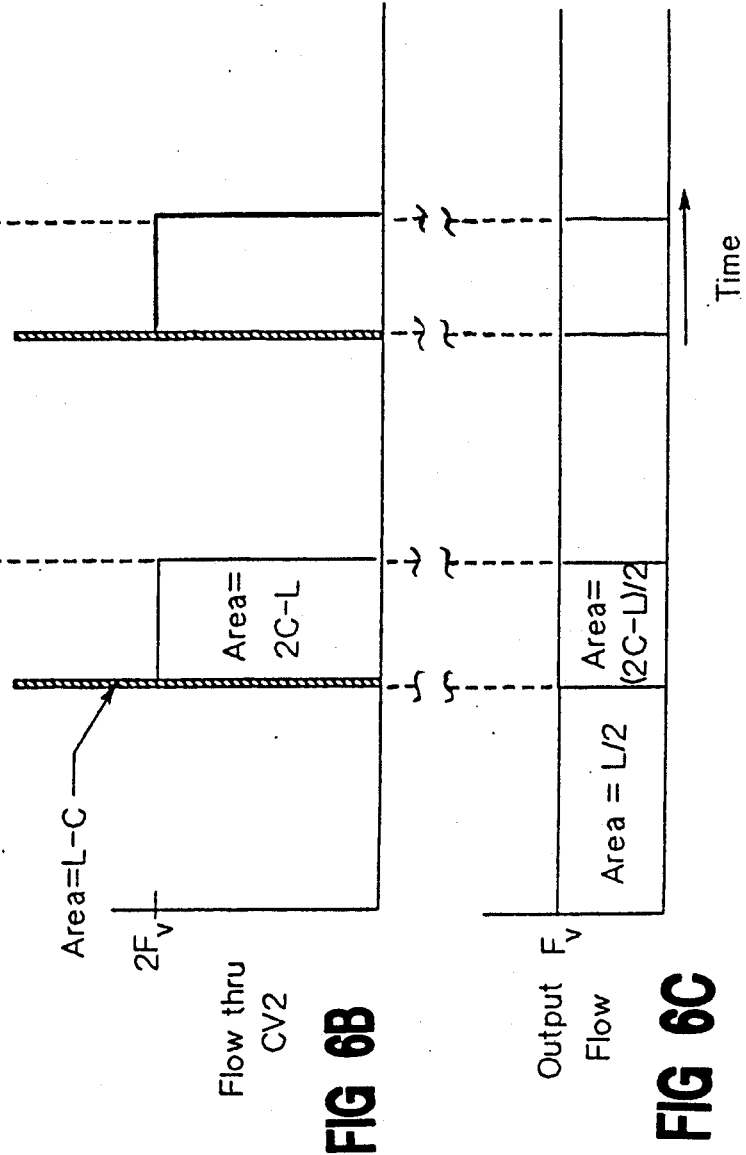

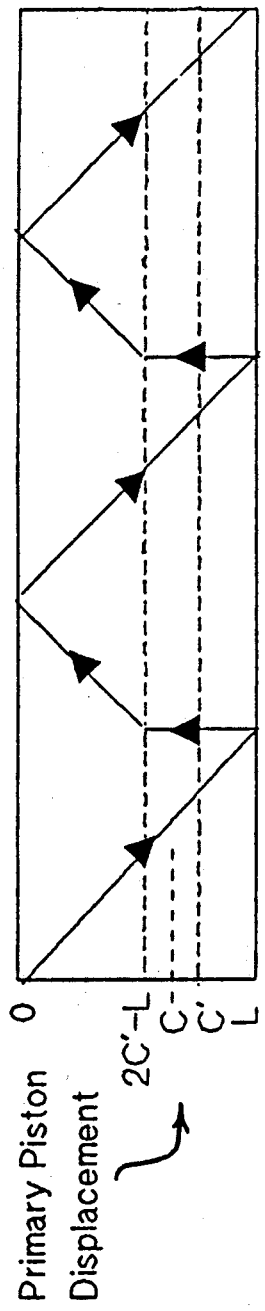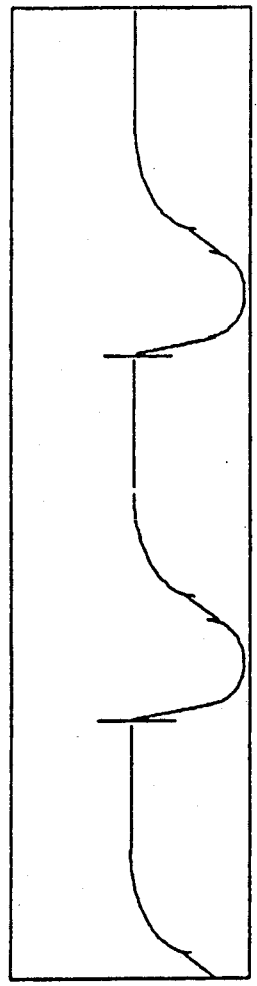
FIG 9A — Primary Piston Displacement
FIG 9B — Carbon dioxide flow pattern observed with adiabatic Compensation C'

PRESSURE & FLOW PATTERN FOR $CO_2$

METHOD AND APPARATUS FOR REAL TIME COMPENSATION OF FLUID COMPRESSIBILITY IN HIGH PRESSURE RECIPROCATING PUMPS

BACKGROUND OF THE INVENTION

The invention relates to a pumping apparatus for delivering liquid at a high pressure, in particular a pumping apparatus for solvent delivery in liquid chromatography or supercritical fluid chromatography. The pumping apparatus pumps a mobile phase and a sample to be separated through the chromatographic system which includes a separation column and various transfer lines.

In chromatographic analysis, the flow rate of the liquid delivered to the column should be adjustable over a wide range. Once adjusted, it is very important to keep the flow rate constant as fluctuations cause variations in the retention time and associated areas under chromatographic peaks generated by chromatographic detectors of the separated sample. Flow sensitive detectors used in supercritical fluid or liquid chromatography include RI detectors, dielectric constant detectors, electrical conductivity detectors, NPD, ECD and fluorescence detectors. Since the area under the peaks are representative of the concentration of the chromatographically separated sample substances, fluctuations in the flow rate would impair the accuracy and the reproducibility of quantitative measurements. Additionally, many detectors are sensitive to flow and/or pressure ripples.

The compressibility of chromatographic solvents becomes noticeable at the high pressures encountered in high performance liquid chromatography and supercritical fluid chromatography. Such compressibility results in an additional source of fluctuations in the flow rate as the piston must compress the liquid to its final delivery pressure before actual delivery of liquid starts. This results in the outflow having pulsations which occur at the frequency of the pump. The percent magnitude of pulsations remains substantially constant over a wide range of flow rates, however, as the amplitudes of the peaks in the chromatogram become smaller at low flow rates, the influence of pulsations on the chromatographic results is more pronounced.

It is known to use a dual piston pump having two interconnected pump heads each with a reciprocating piston. The pistons may be driven via cams and a camshaft, a ball-screw drive or any other suitable mechanism which permits a phase difference resulting in a comparatively smooth outflow. A dual piston pump driven via cams and a common cam shaft is known from U.S. Pat. No. 4,352,636. One type of reciprocating pump which incorporates the ball-screw drive is disclosed in U.S. Pat. No. 4,883,409 entitled "Pumping Apparatus for Delivering Liquid at High Pressure", and is hereby incorporated by reference. As set forth in FIG. 1 the '409 patent discloses a pumping apparatus having two gear driven pistons which reciprocate in opposite directions in two pump chambers, respectively. The pistons are coupled to ball-screw drives which translate the rotary motion of the spindles into a linear motion of the pistons. The stroke volume can be changed by changing the amount in which the spindles are rotated during a pump cycle. Furthermore, a ball-screw drive permits the selection of any desired piston displacement over time during a pump cycle. For example, the displacement may be varied linearly as a function of time or accelerated for a short time to obtain a pre-compression phase.

FIG. 2(a) illustrates the beginning of the intake cycle for a known ball-screw, dual chamber reciprocating pump illustrated in FIG. 1 in which the output of the primary pump chamber is connected via a valve to the input of the secondary pump chamber. The stroke of each piston can be varied by controlling the angle of rotation of a reversible drive motor. The gear ratio is chosen to allow the primary piston to sweep twice as much volume as the secondary piston. If the primary and secondary cylinders have the same diameter, then the primary piston must move twice as fast as the secondary piston. Thus, if the primary piston has a volumetric stroke of L, the secondary piston will have a volumetric stroke of L/2. The outlet pressure can be kept constant at $P_o$ using a back pressure regulator or a flow restrictor.

The pumping cycle for this pump is set forth in FIG. 2(b). As the primary piston moves downward, the primary pressure decreases causing check valve 10 to open and check valve 20 to close, thus sucking in a fluid volume equal to L from the inlet. At the same time, the secondary piston delivers a volume of liquid (L/2) to the outlet. The pump motor then changes direction and the primary piston moves upward delivering a volume L. One half of this volume (L/2) is delivered to the outlet, and the other half is used to fill the vacuum generated in the secondary cylinder due to its downward motion. Assuming the fluid is incompressible, a flow of L/cycle is maintained in accordance to FIG. 3(a)-3(d). The volumetric flow rate $F_v$ for incompressible fluids can be expressed as follows:

$$F_v = L \times f_i \qquad \text{(Volume per unit time)} \quad \text{Eqn (1)}$$

Where:
 $F_v$ = Volumetric flow rate at a defined outlet pressure
 $f_i$ = Pump frequency in cycles per unit time required to maintain flow rate of $F_v$ when pumping incompressible fluids.
 L = Primary piston stroke volume The mass flow rate $F_m$ can be expressed as:

$$F_m = \rho_i \times F_v = \rho_i \times L \times f_i \qquad \text{(Mass per unit time)} \quad \text{Eqn (2)}$$

Where:
 $\rho_o$ = Fluid density at the outlet pressure. Assumed constant for incompressible fluids at all pressures and temperatures.

Since real fluids are compressible, Eqn 1 and Eqn 2 do not correctly set forth the volumetric flow rate and mass flow rate of a reciprocating pump. Furthermore, the compressibility of the fluid is a function of both pressure and temperature. Liquid chromatography and supercritical fluid chromatography systems typically treat these compressibility factors as constants, however, they vary considerably.

SUMMARY OF THE INVENTION

In accordance with this invention, a method and apparatus are described for significantly improving the performance of a reciprocating pump by delivering the pumping fluid at a desired pressure and flow rate with minimal flow fluctuations. The method includes the step of sensing various pump parameters and adjusting the pumping speed to accommodate for the compressibility of the pumping fluid, the adiabatic heating of the pumping fluid during compression, variations in pumping fluid density, leaks in the check valves or cylinder/piston seals and the primary and secondary switching losses in the fluid flow occurring when the piston reverses direction. The compressibility of the pumping fluid directly effects volumetric flow rate and mass flow rate. These effects are much more noticeable when using supercritical fluids such as $CO_2$ than in other liquids. The assumption of a constant compressibility leads to optimal minimization of fluid fluctuation at only one point of the pressure/temperature characteristic. At other pressures and temperatures, flow fluctuations due to overcompensation or under-compensation becomes apparent. Accordingly, the object of the invention is to significantly reduce pumping and flow noise in reciprocating pumps by taking into account the pressure and temperature dependency of the compressibility of the pumping fluid.

The compression stroke of the pumping cycle is not isothermal as the rapid compression of the fluid causes a significant increase in fluid temperature. The density and the mass flow rate also vary with fluid temperature. This results in a positive flow pulse passing to the outlet and results in a flow ripple. To eliminate flow variations caused by temperature variations, the pumping fluid in the primary cylinder which is normally compressed to a volume C, is compressed to a different volume C'. The value of volume C' is larger than volume C and is calculated so that the fluid reaches the system pressure at the increased temperature and at a constant mass flow rate. Accordingly, it is another object of the invention to decrease the flow variations by taking into account the cyclic increase in temperature caused by the fluid compression.

The use of very low pumping flow rates is becoming more popular in liquid chromatography. When using a reciprocating pump at very small flow rates, leaks may form at the check valves or cylinder/piston seals. Identifying these leaks and compensating for them is extremely important when pumping supercritical fluid modifiers as it directly affects the mixing of the modifier in the CO2. Therefore, another object of the invention is to compensate for such leaks by measuring the flow with a high pressure flowmeter and increasing the pump speed of either the primary or the secondary piston or both pistons till the expected flow rate is achieved.

A secondary ripple in the fluid flow occurs when the piston reverses direction at the top of the stroke as some fluid escapes through the secondary check valve to the primary piston (secondary valve switching loss). It is another object of the invention to compensate for this secondary ripple by injecting a small volume of liquid in addition to the steady flow amount. The calculated value C'(new volume) is found to be larger from the measured empirical value due to the primary valve switching loss. The invention corrects the problem by continuously monitoring the pressure and adjusting the C' value to maintain a minimum pressure ripple. The difference between the calculated C' and the optimum measured C' establishes the switching loss in the primary valve. After the compression stroke, the fluid density in the primary cylinder increases as the fluid cools down to the temperature of the pump wall. This causes the mass flow and pressure to vary during the pumping cycle. Therefore, another objective of the invention is to modulate the pump speed so as to achieve constant mass flow rate and constant pressure.

BRIEF DESCRIPTION OF DRAWINGS

The present invention may be better understood, and its numerous objects and advantages will become apparent to those skilled in the art by reference to the accompanying drawings of which:

FIG. 5(a), 5(b) and 5(c) are fluid displacement and flow patterns of a compressible fluid.

FIG. 6(a), 6(b) and 6(c) illustrates the flow pattern for compressible fluids in which compensation for compressibility is employed.

FIG. 9(a) and 9(b) represent the primary piston displacement and corresponding flow pattern observed with supercritical $CO_2$ with adiabatic compensation C' and constant volumetric flow rate.

DESCRIPTION OF THE PREFERRED EMBODIMENT

In the preferred embodiment, a fluid pump as described in U.S. Pat. No. 4,883,409 is modified to provide for sensing various pump parameters and adjusting of the pumping speed, such that fluctuations in the pumping pressure and mass flow rate are reduced.

Figure 1:
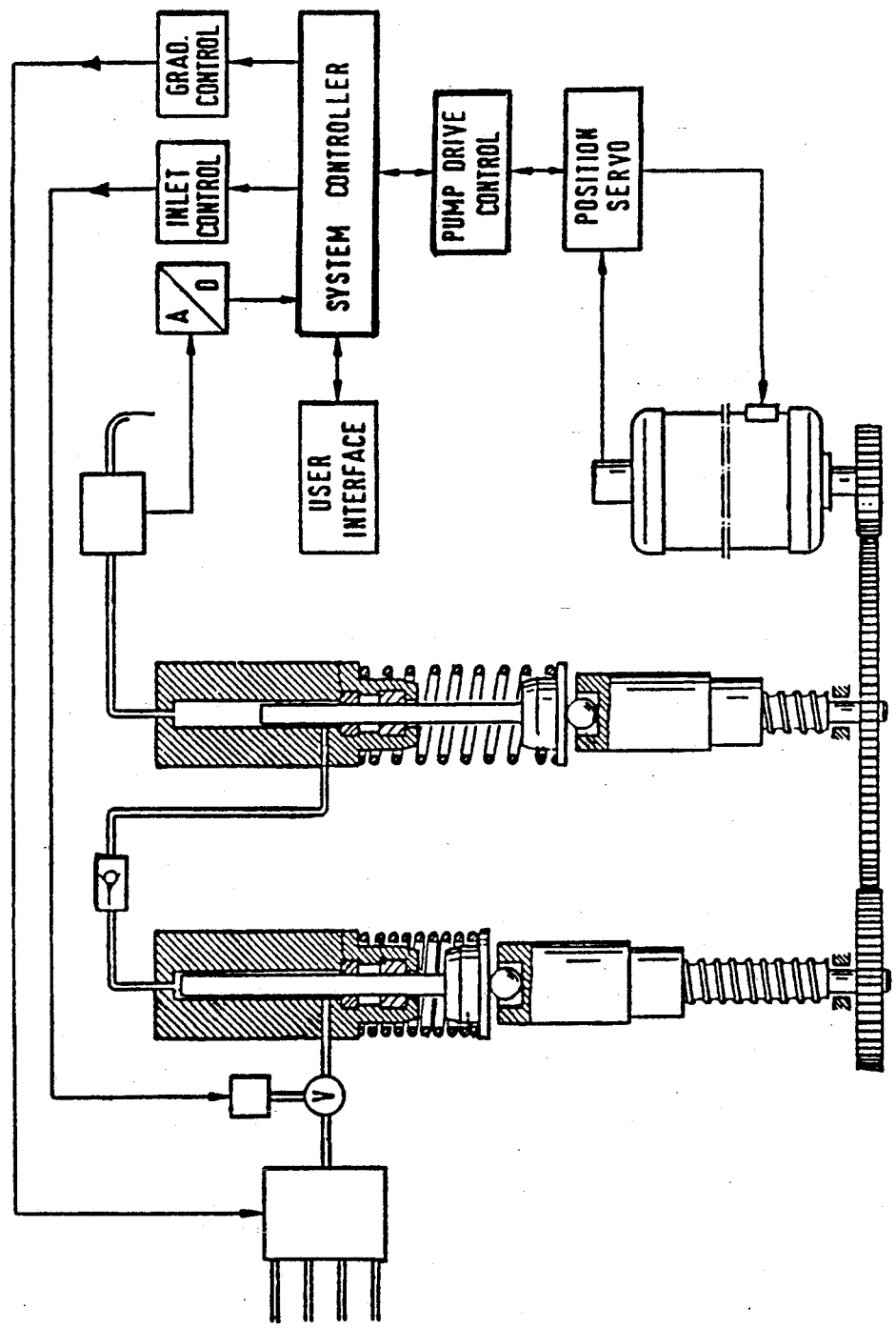
FIG. 1 is a diagram of the Prior Art pumping apparatus.
Figure 2A:
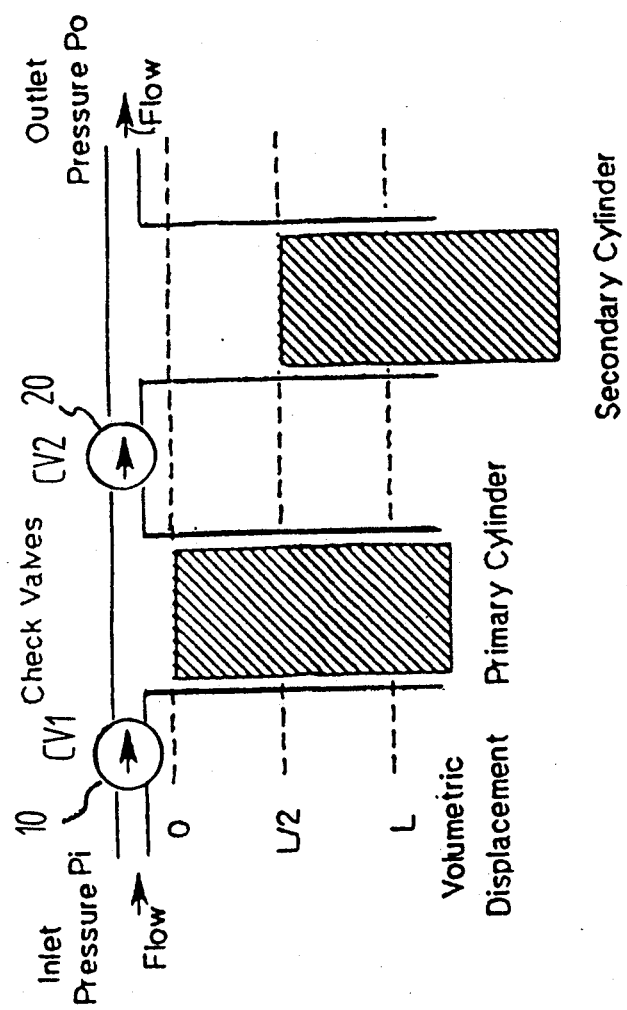
FIG. 2(a) and FIG. 2(b) are diagrams illustrating the primary and secondary piston positions during the pumping cycle.
Figure 2B:
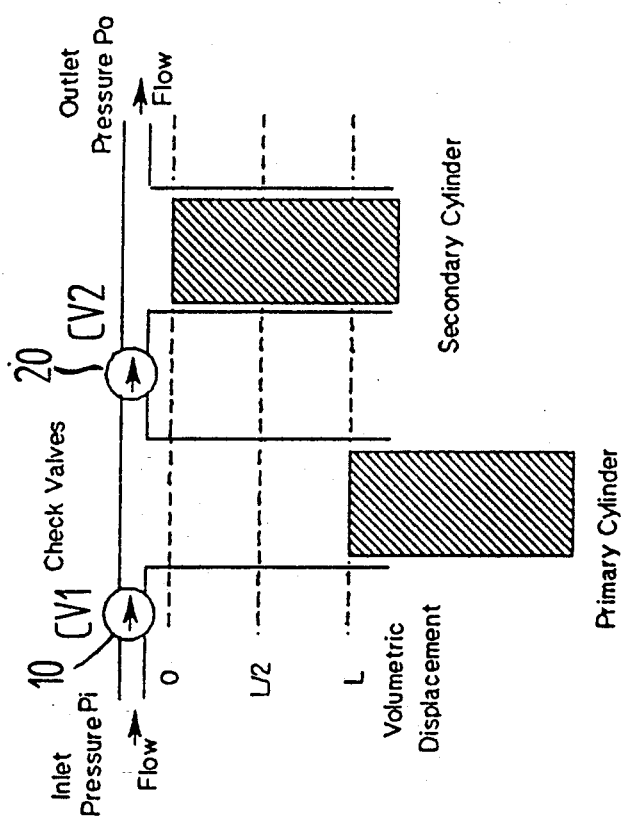
Figure 3A:
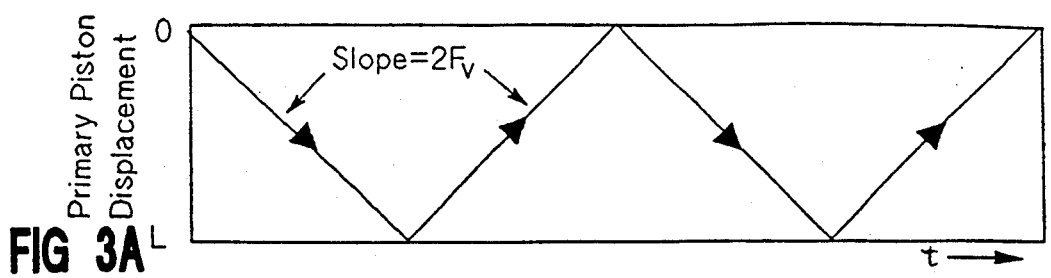
FIG. 3(a), 3(b), 3(c) and 3(d) are fluid displacement and flow patterns through the pump for ideally incompressible fluids.
Figure 3B:
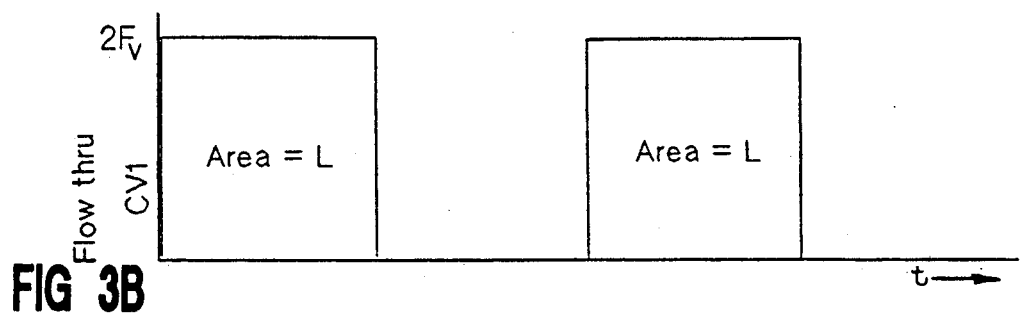
Figure 3C:
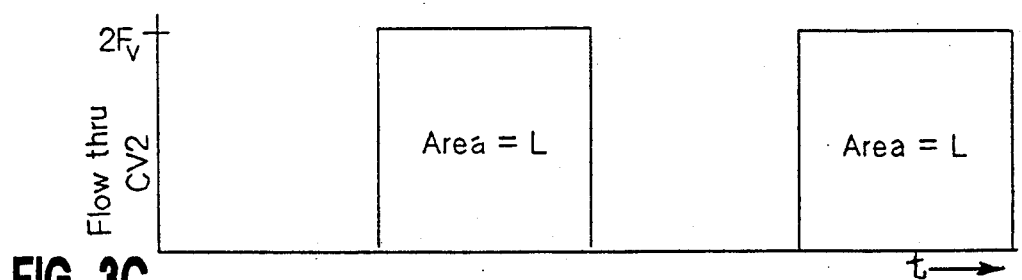
Figure 3D:
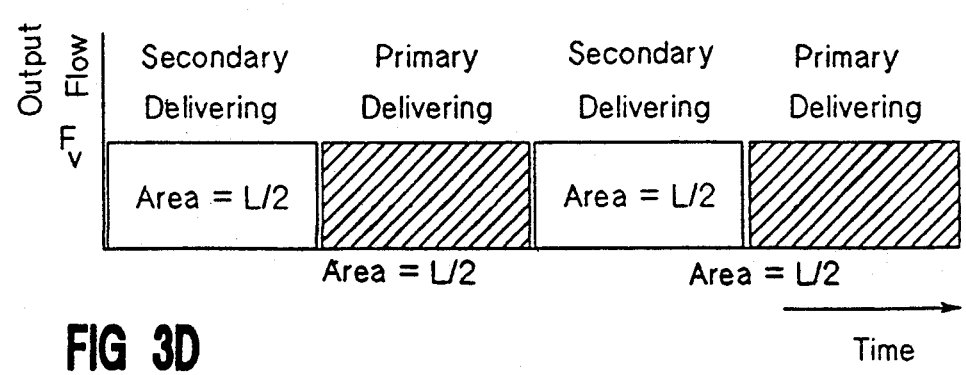
Figure 4A:
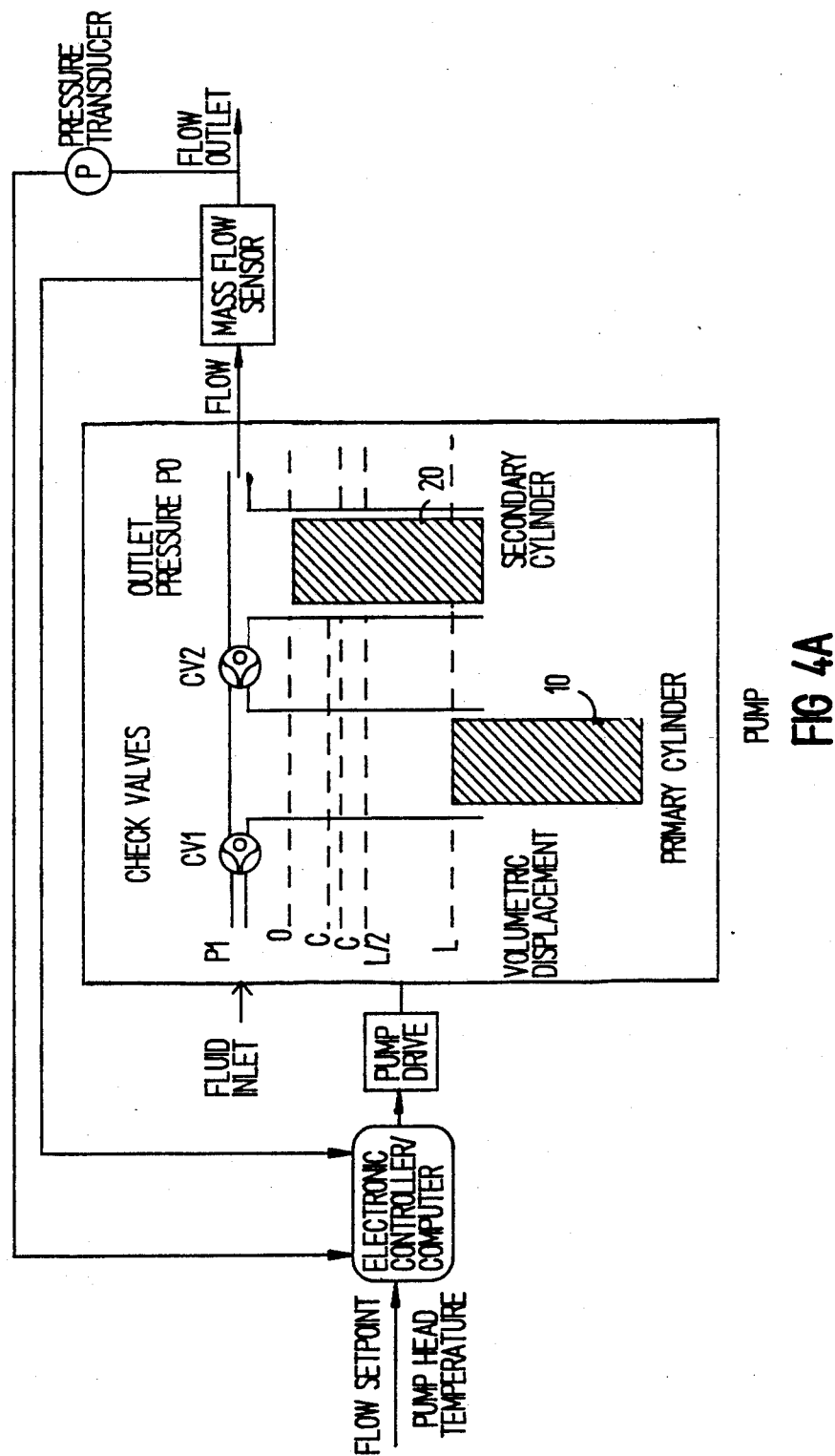
FIG. 4(a) and 4(b) are block diagrams of the invention in is which different levels of sensing devices are employed for generating feedback signals.

In particular, FIG. 4(a) illustrates the addition of mass flow sensors, pump head temperature sensors, inlet and outlet pressure sensors, all of which provide feedback to an electronic pump speed controller. The pump drive motor rotation angle, and the corresponding stroke of the two pistons (10,20), is controlled by firmware running on a microprocessor to accommodate for the compressibility of the pumping fluid, the adiabatic heating of the pumping fluid during compression, variations in pumping fluid density, leaks in the check valves CV1 and CV2 or cylinder/piston seals and the primary and secondary switching losses in the fluid flow occurring when the piston reverses direction.

FIGS. 5 illustrates the flow patterns for compressible fluids as a function of primary piston displacement, flow through CV2 and the volumetric output flow $F_v$. In the primary delivery stroke, the primary piston moves upward to a calculable position C before the pressure in the primary cylinder increases from the initial intake pressure $P_i$ to the outlet pressure $P_o$. A negative flow from the outlet, which is ideally maintained at a constant pressure, to the pump will occur during the compression displacement. The reduced average volumetric flow rate at an uncompensated outlet pressure $F_v$ equals $C \times f$. In order to compensate for reduced and discontinuous flow, the pump motor is instructed to quickly compress the fluid upon intake by moving the primary piston twice the displacement needed to reach the outlet pressure using the maximum speed possible. As set forth in FIG. 6, the primary piston will quickly move from position L to a new position defined as:

$$\text{Compensation position} = C - (L - C) = 2C - L \quad \text{(Eqn (3))}$$

FIG. 6 (c) shows the resulting flow patterns. The pump frequency has been increased by a factor of L/C to make up for the reduced flow and is defined as:

$$\text{New pump frequency } f = (L/C) \times f_i \quad \text{(Eqn (4))}$$

By compensating for the fluid compressibility, the flow rate is returned to that of the incompressible fluid, where:

$$F_v \text{ (compensated)} = C \times f = C \times (L/C) \times f_i \quad \text{(Eqn (5))}$$
$$= L \times f_i$$

In an ideal pump, the temperature of the pumping fluid can be assumed to stay constant when the primary piston moves from position L to position C. Additionally, the mass of the fluid in the primary cylinder stays constant such that:

$$(D + L) \times \rho_i = (D + C) \times \rho_o \quad \text{Eqn (6)}$$

Or:

$$\frac{D + L}{D + C} = \frac{\rho_o}{\rho_i}$$

Where:
D = Primary piston dead volume
L = Primary volumetric stroke
C = The primary piston position at which the primary cylinder pressure has just reached the outlet pressure $P_o$ (unknown)
$\rho_i$ = Fluid density right after the intake stroke (density at inlet pressure)
$\rho_o$ = Fluid density right after the compression stroke (density at outlet pressure)

Figure 8A:
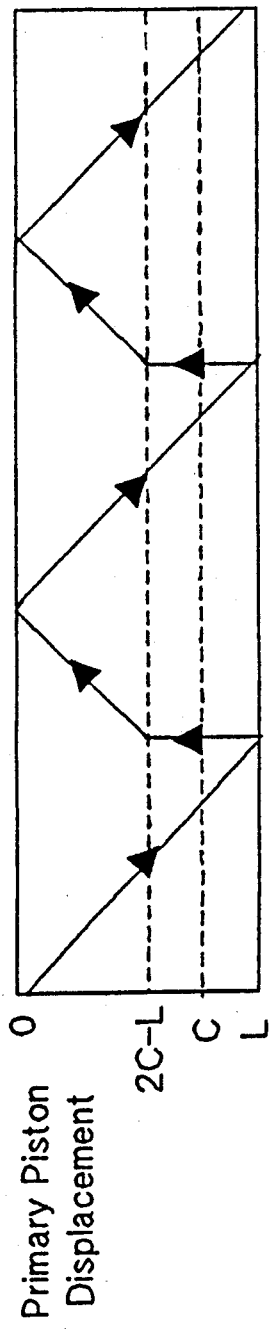
FIG. 8(a) and 8(b) represent the primary piston displacement and corresponding flow pattern observed with supercritical $CO_2$ with compression value calculated assuming isothermal compression. This is the actual output of a prior art pump which illustrates fluctuations in fluid flow.
Figure 8B:
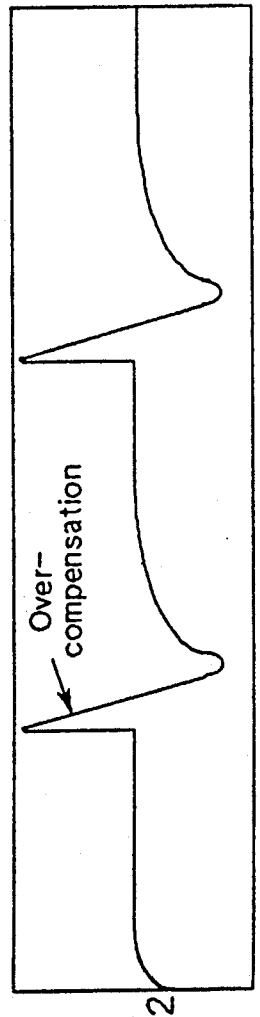

Both $\rho_i$ and $\rho_o$ can be obtained from the equations of state of the specific fluid employed. When compressed, the pumping fluid heats up and attempts to expand such that the outlet pressure is reached prior to the piston moving to the volume C. This effect causes a fast positive flow pulse to pass to the pump outlet (FIG. 8b). Right after the compression stroke, the mass flow rate will be less than the calculated value due to decreased fluid density. The mass flow rate will continue to increase according to the time constant of heat exchange between the fluid and pump body. The resulting flow waveform due to this phenomena is shown in FIG. 8B. This effect is more dramatic in fluids having high compressibility such as supercritical compressed gases. For supercritical carbon dioxide at outlet pressures above 200 bar, temperature rise of more than ten degrees centigrade have been calculated and empirically validated.

Figure 10:
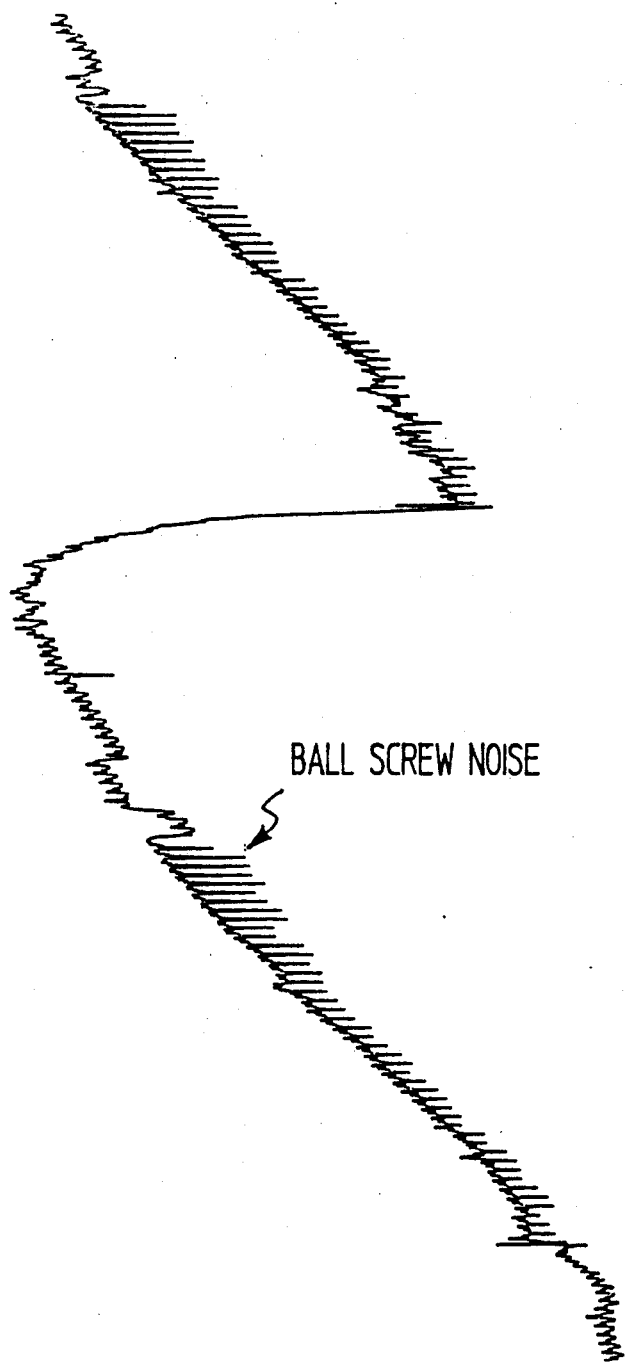
FIG. 10 is an actual pump output of FIG. 9(b) showing flow fluctuations and ball screw noise.

In order to overcome and virtually eliminate this large flow ripple, the fluid in the primary cylinder is compressed to a different volume C'. The value of C' is larger than C and is calculated so that the fluid reaches system pressure at an increased temperature. The primary piston is moved farther by the same displacement (to volume 2C' − L) in order to fill the vacuum created in the secondary cylinder FIG. 9A. For carbon dioxide with adiabatic compensation, this will result in the flow waveform shown in FIG. 9(b) and the actual plot of FIG. 10.

The pump speed is also programmed to ensure constant mass flow by accounting for the lost flow due to decreased density, and the elimination o flow ripple due to varying density. In particular, the post-compression temperature is first expressed as a function of time such that the fluid density can be represented as a function of time. From this equation, the piston speed required for constant mass flow can be derived.

Since the rapid compression of the pumping fluid causes the fluid to heat up and expand, the density decreases. When heat is transferred to the pump body, the pumped fluid cools and the density increases. The rate of density variation can be determined using the time function f(t) of heat exchange between the fluid in the pump and its surroundings.

For constant mass flow rate:

$$\frac{d[V(t) - \rho(t)]}{dt} = -f \quad \text{Eqn (7)}$$

$$V(t)\frac{d\rho(t)}{dt} + \rho(t)\frac{dV(t)}{dt} = -f$$

P(t) can be approximated by the following function:

$$\rho(t) = \rho_i + (\rho_f - \rho_i)(1 - e^{-t/\tau})$$

$\rho_i$ = initial fluid density right after the fast compression stroke
$\rho_f$ = final density at steady state pump temperature and outlet pressure
t = time
$\rho(t)$ = fluid density as function of time
V(t) = pump volume filled with fluid at outlet pressure
$\tau$ = thermal time constant of heat exchange between the fluid and the pump walls. ~3 seconds
f = required mass flow rate Solve Eqn (7) for $$\frac{dV(t)}{dt}$$

which is the volumetric flow rate (piston speed)

For any fluid, entropy "s" is a function of pressure and temperature. This can be expressed as:

$$s = s(P, T) \quad \text{Eqn (8)}$$

Therefore a constant entropy curve can be expressed as:

$$s(P, T) = \text{constant} \quad \text{Eqn (9)}$$

Fluid temperature and pressure at point L as illustrated by the piston position of the pump in FIG. 4(a) are known (pump head temperature and inlet pressure). At point C', pressure is equal to outlet pressure and temperature is unknown.

Thus, we can write:

$$s(P_o, T_c) = s(P_i, T_l) \quad \text{Eqn (10)}$$

The only unknown in Eqn 10 is the compression temperature $T_c'$. After solving for $T_c'$, one can substitute $T_c'$ in the fluid equation of State:

$$P = P(\rho, T) \quad \text{Eqn (11)}$$

and find the new density at this point C' ($P_{c'}$). Density and entropy look-up tables for the specific fluid can be used as well as the equations of state for this fluid. Using a "universal" equation of state may be preferable as it can apply to many different fluids and can simplify computer mathematical manipulations.

The value of C' can be found from the equation:

$$\frac{D + L}{D + C'} = \frac{\rho_{c'}}{\rho_L} \quad \text{Eqn (12)}$$

Figure 11A:
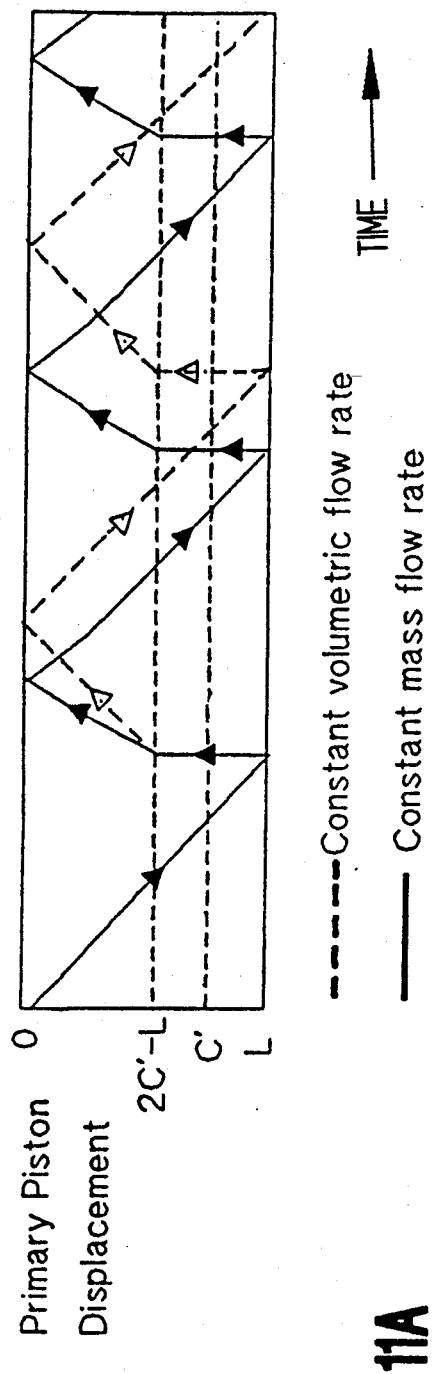
FIG. 11(a) illustrates the relationship between primary piston displacement, constant volumetric flow rate and constant mass flow.
Figure 11B:
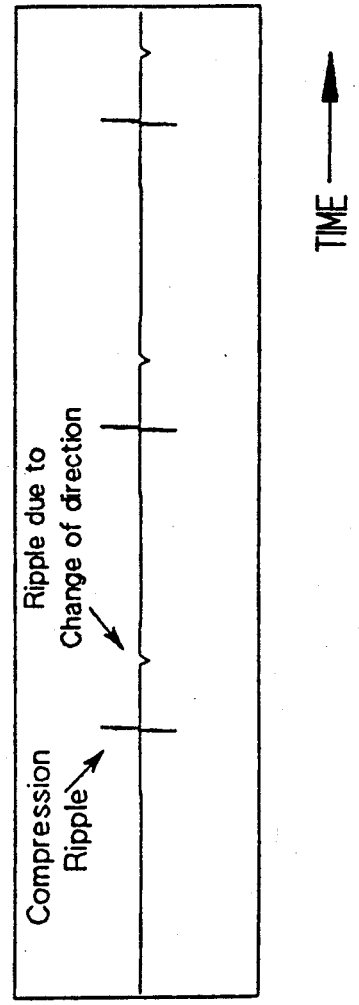
FIG. 11(b) illustrates the pressure and flow pattern for a carbon dioxide using adiabatic compensation C' and programming volumetric flow so as to maintain a constant mass flow rate.
Figure 12:
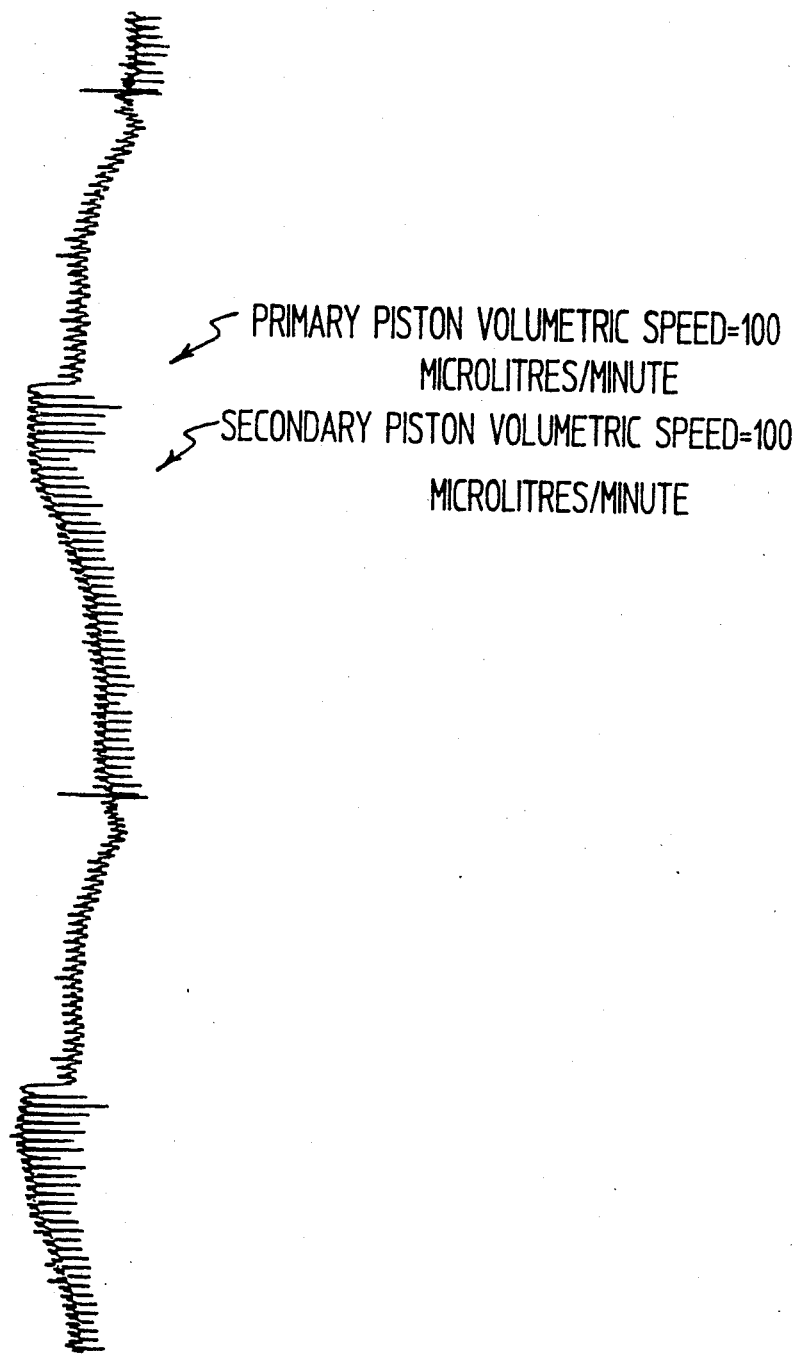
FIG. 12 is the actual pump output of FIG. 11(b).

FIG. 11(a) illustrates the relationship between primary piston displacement, constant volumetric flow rate and constant mass flow rate. FIG. 11(b) illustrates the flow pattern for carbon dioxide using C' and programming volumetric flow so as to maintain constant mass flow rate.

Figure 13A:
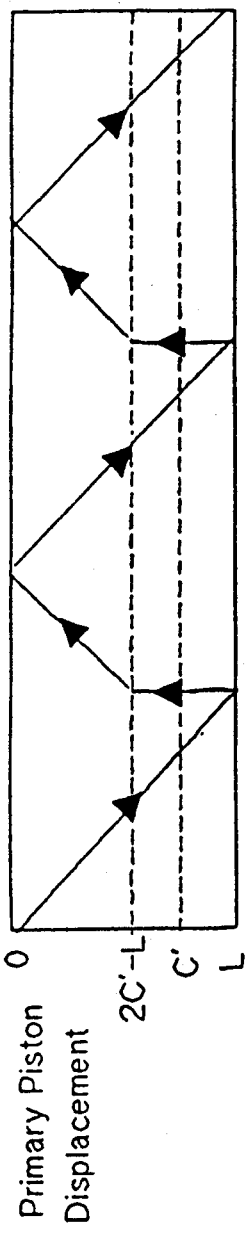
FIG. 13(a), 13(b), 13(c) and 13(d) illustrate very low flow patterns for the pump with an unbalanced at a constant outlet pressure and the pressure and flow pattern after leak correction.
Figure 13B:
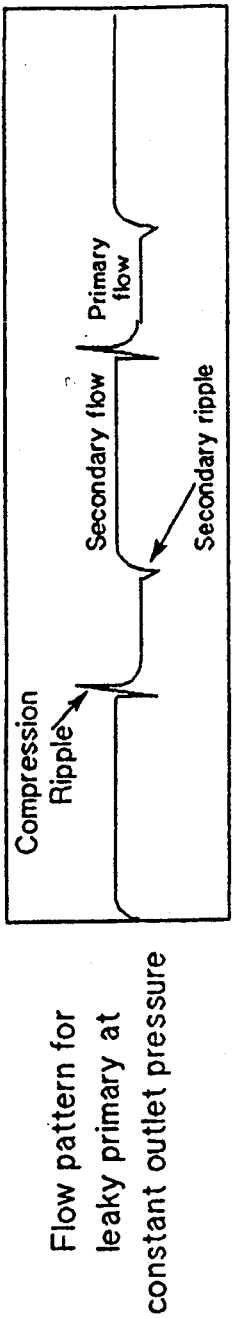
Figure 13C:
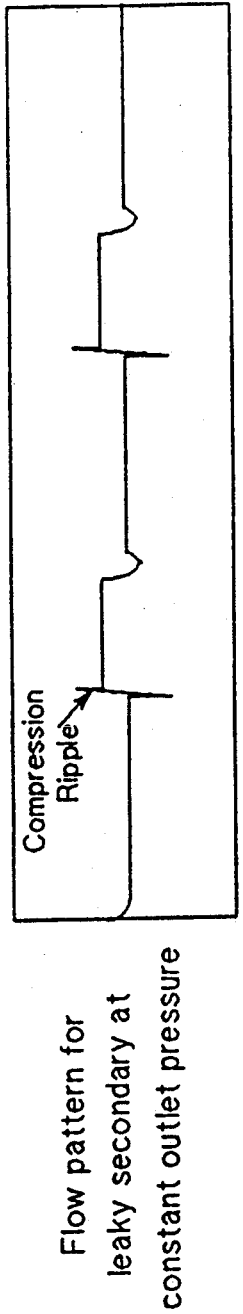
Figure 13D:
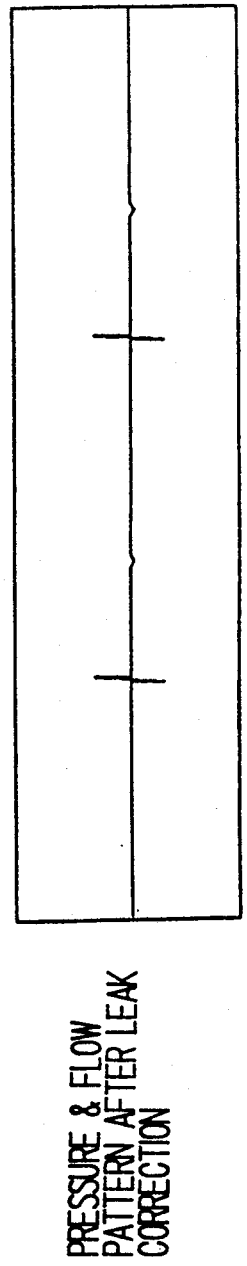

At very low flow rates, leaks may form through check valves or cylinder/piston seals. Absolute flow correction can be made by measuring the flow rate with a high pressure flowmeter and increasing the pump speed till the expected flow rate is achieved. If either side is leaking more than the other, then the flow will be uneven during each associated pump cycle. This leads to flow ripple as illustrated in FIG. 13(b) and FIG. 13(c). This ripple can be minimized by increasing the speed of the piston on the side which is leaking until a steady flow is obtained (FIG. 13(d). In addition to smoothing out the ripple, this technique also corrects the absolute flow as the actual flow of the more leaky side is increased to that of the less leaky side.

Figure 14A:
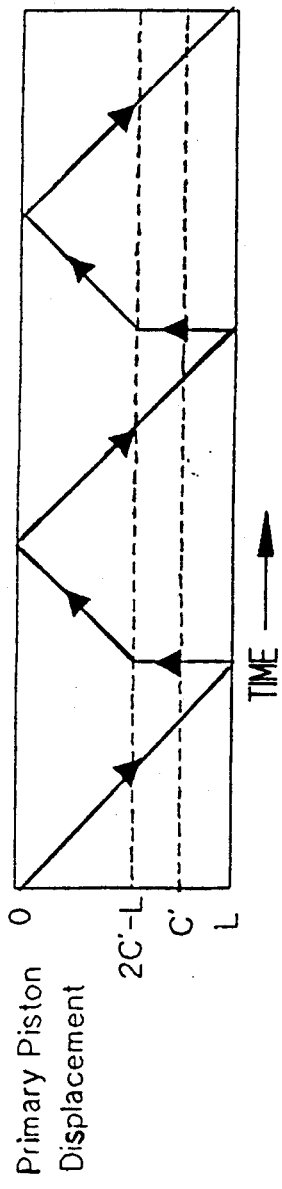
FIG. 14(a), 14(b), 14(c) and 14(d) illustrate the pressure patterns for both a leaky primary and secondary when using a fixed restrictor and after leak correction.
Figure 14B:
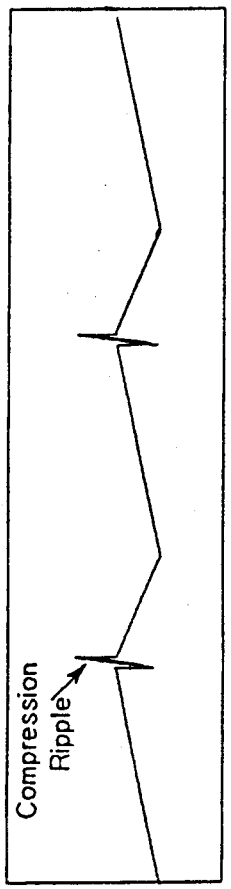
Figure 14C:
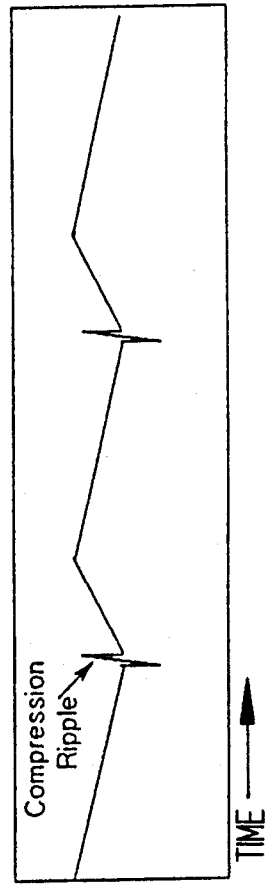
Figure 14D:
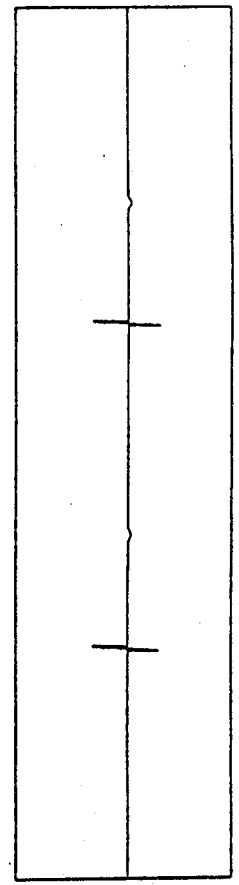
Figure 15:
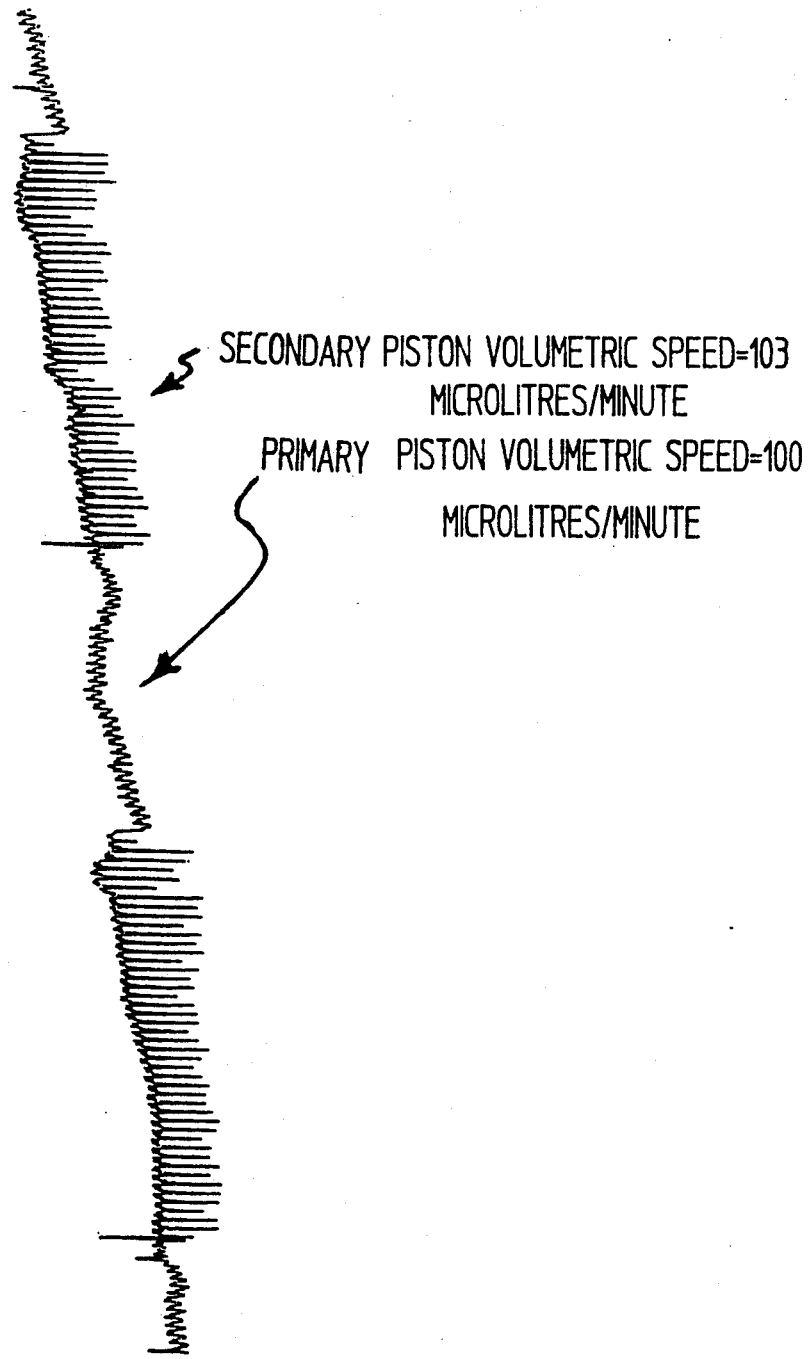
FIG. 15 is the actual pump output of FIG. 14(d).

In another embodiment which does not use a high pressure flowmeter, the differential leak flow ripple can be minimized by pumping fluid into a fixed restrictor whose value is chosen to obtain about the same outlet pressure and the required flow rate. FIGS. 14(b) and 14(c) illustrate the pressure patterns for both a leaky primary and secondary when using a fixed restrictor. The outlet pressure is monitored and analyzed by a microprocessor to indicate which side is leaking the most such that the corresponding piston can be moved faster to correct for the pressure ripple. FIG. 14(d) illustrates the pressure and flow patterns after leak correction. FIG. 15 is the actual plot of FIG. 14(d).

Figure 4B:
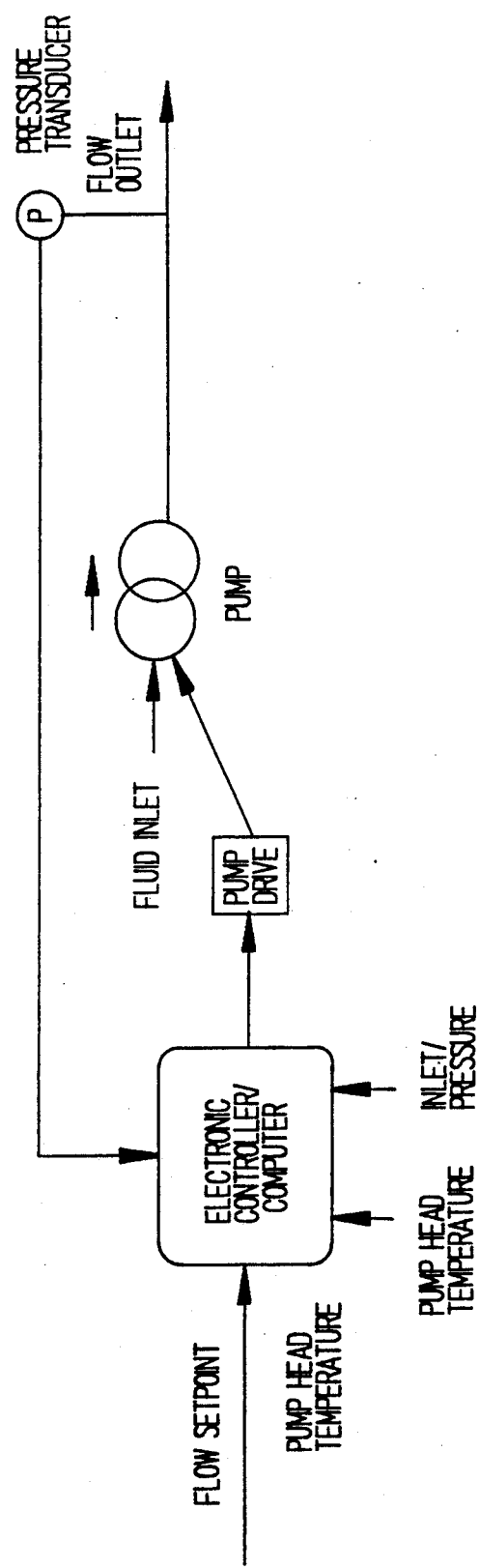
Figure 7A:
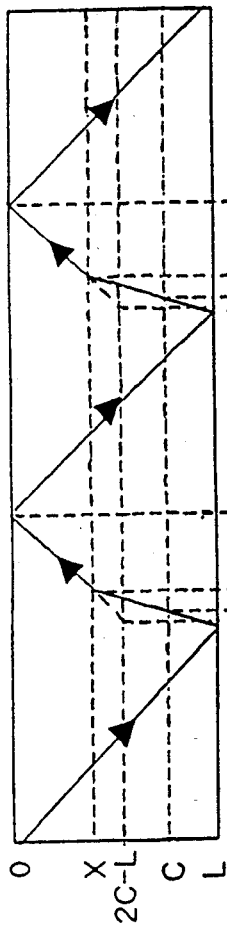
FIG. 7(a), 7(b) and 7(c) illustrate the flow pattern for compressible fluids in which compensation for compressibility is employed but with finite pump motor speed.
Figure 7B:
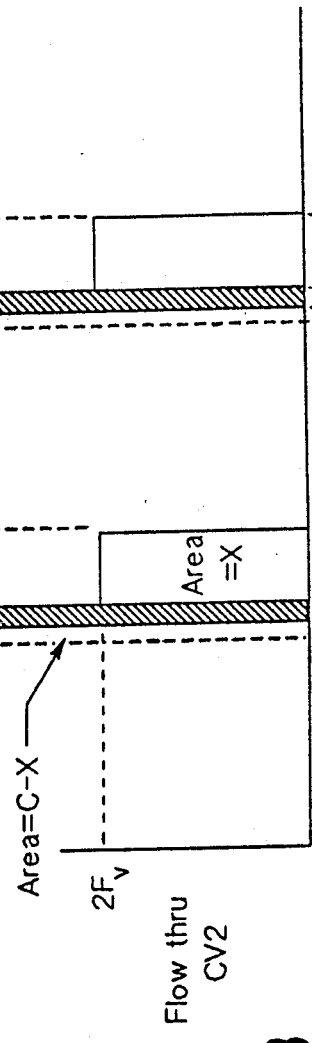
Figure 7C:
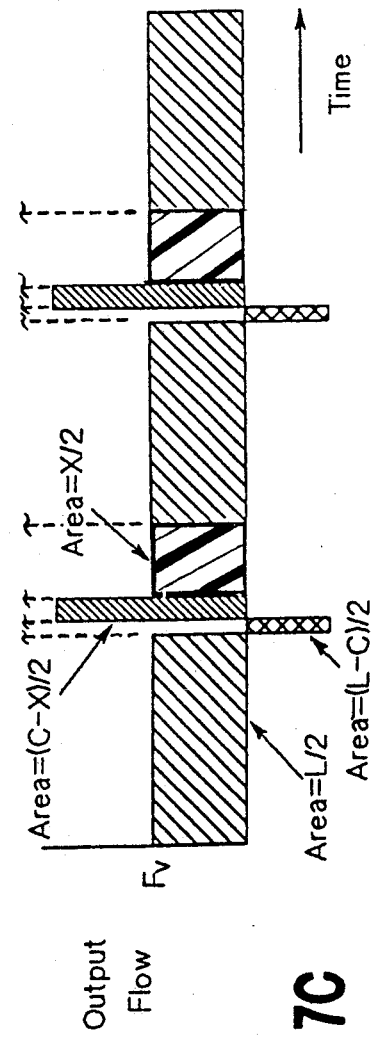

Secondary ripple is a negative ripple due to the flow lost when the pistons change direction as the secondary starts pumping, and is particularly apparent with small flow rates. Injecting an additional volume of liquid during the pumping cycle compensates for this secondary ripple and smooths out the flow rate. The injection is performed by setting the pump speed to the maximum speed allowed for a very short time right after the piston changes direction. The amount of fluid mass to be injected can be estimated using the area of the negative ripple in the flow diagram. A simplified block diagrams illustrating a feedback loop incorporating a pressure and flow transducer are set forth in FIG. 4. While examining the output of the mass flow sensor or the pressure transducer, adjustments can be made to the pump drive to minimize the flow ripple.

Figure 16:
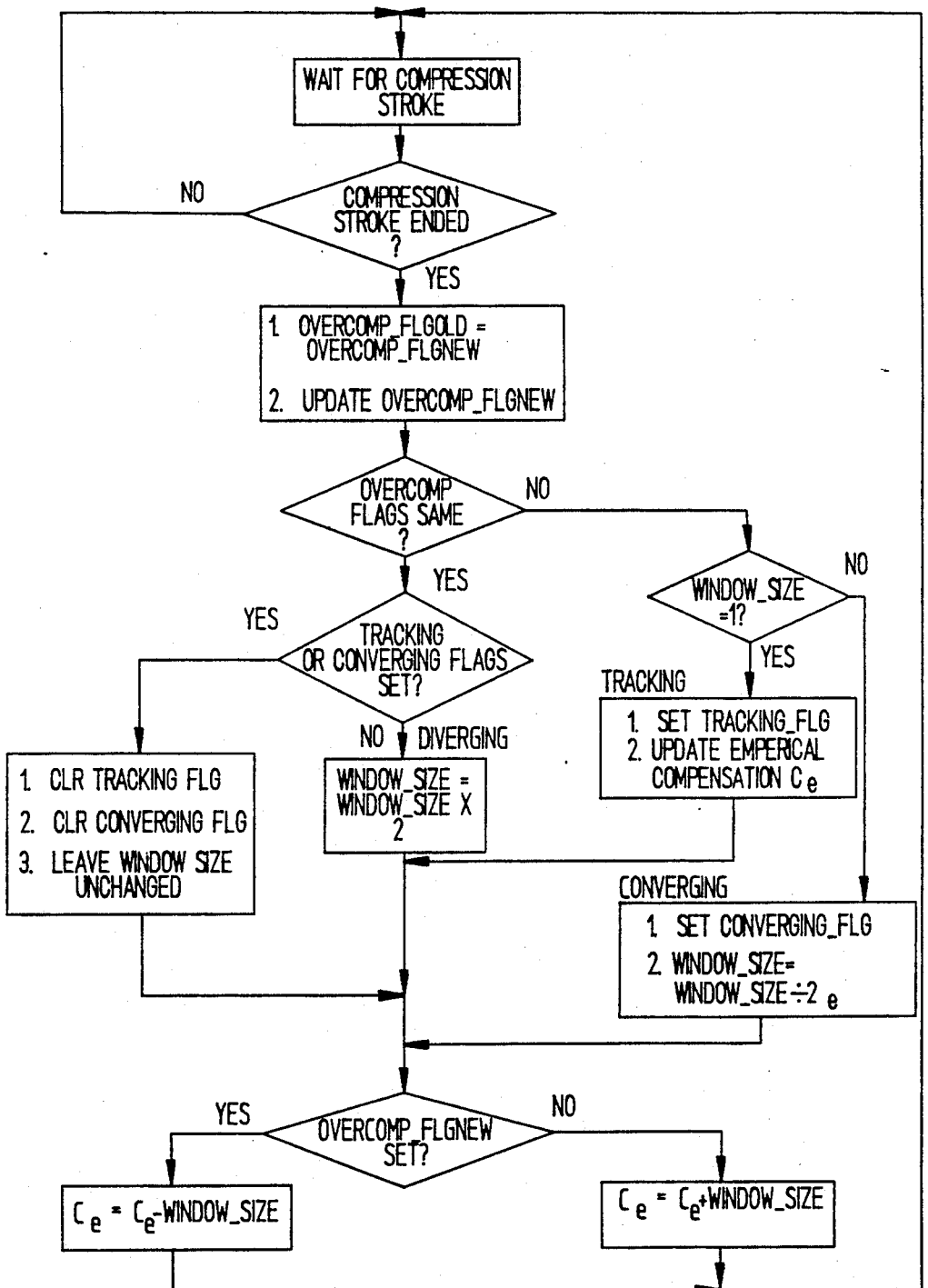
FIG. 16 is a flow chart of the compression tracking algorithm.

The invention also provides for automatically compensating for primary valve switching loss by continuously monitoring the pressure waveform and changing compressibility compensation to maintain the desired pressure. By analyzing the pressure waveform, firmware can detect under-compensation and over-compensation and increase or decrease the amount of compensation accordingly. FIG. 16 is a flowchart illustrating how the system works, and in particular, the following three general steps required for automatic compensation of primary valve switching loss:

1) Initially, the empirical compensation $C_e$ is set to equal the theoretically calculated value C'.

2) A volumetric "window unit" is entered, for example, 0.1 micro-liter.

3) A control loop is entered and repeats itself every cycle starting after the compression stroke.

The control loop includes a system which diverges if neither of the tracking or converging flags are set and there is no compensation reversal (this indicates that the direction of the compensation has changed from the last cycle). In this case, the window is opened up to twice its previous size. Compensation $C_e$ is then increased or decreased by the window size if the system was under-compensated or over-compensated respectively.

The system is determined to be converging on the target if there is compensation reversal and the window size is greater than one. In this case the window gets closed to half its previous size. Compensation $C_e$ is increased or decreased by the window size if the system was under-compensated or over-compensated respectively. The converging flag is then set.

The system is determined to be on track of the target if there is compensation reversal and the window size is set to one. In case of over compensation, the compensation value $C_e$ is decreased by on window unit. In case of under compensation, $C_e$ is increased by one window unit. Tracking flag is set.

If the tracking flag is set and there was no compensation reversal, the flag is cleared and the window size is left unchanged in order to smoothly control slow target drift while tracking.

If the converging flag is set and there was no compensation reversal, the flag is cleared and the window size is left unchanged in order to converge successfully.

Although the best results are obtained by the forgoing pumping method and apparatus, changes and modification of the invention, as set forth in the specifically described embodiments, can be carried out without departing from the scope of the invention which is intended to be limited only by the scope of the appended claims.

I claim:

1. A method for delivering a pumping fluid, such as a liquid or supercritical fluid, at a desired pressure and mass flow rate with minimal fluctuations, comprising the method steps of:
   sensing the type of fluid being pumped, the initial piston displacement and initial pressure of the pumping fluid prior to pumping cycle; and
   calculating the amount of additional compression displacement required to compensate for fluid compressibility as a function of the type of fluid being pumped, the initial piston displacement and the initial pressure of the pumping fluid; and
   adjusting the final piston displacement to compensate for the fluid compressibility.

2. The method for delivering a pumping fluid as claimed in claim 1, further comprising the steps of:
   calculating the output density of the pumping fluid at the final piston displacement as a function of the type of fluid being pumped, the initial piston displacement and the initial pressure of the pumping fluid; and
   adjusting the pumping speed to compensate for density changes in the pumping fluid resulting from said temperature and pressure changes such that the fluid is pumped at a desired pressure and mass flow rate with minimal fluctuations.

3. A method for delivering a pumping fluid as set forth in claim 1, further comprising the steps of:
   injecting an additional amount of pumping fluid by increasing the compression stroke for the pumping cycle starting right after the piston changes direction, wherein the amount of liquid escaping from the inlet valve during the rapid compression portion of the pumping cycle is offset to provide constant mass flow rate with minimal fluctuations.

4. A method for delivering a pumping fluid as set forth in claim 3, further comprising the steps of;
   sensing the pumping pressure immediately prior to the rapid piston displacement portion of the pumping cycle and immediately after the rapid piston displacement; wherein, a control loop is entered which adjusts the length of the piston stroke to ensure that the post-compression pressure is equal to the pre-compression pressure.

5. A method for delivering a pumping fluid as set forth in claim 3, further comprises the step of detecting compression under-compensation and over-compensation by comparing the post compression pressure with the pre-compression pressure and increasing the length of the compression stroke by a specific amount if there is under-compensation and increasing the length of the compression stroke by a specific amount if there is over-compensation, thereby ensuring that the desired flow rate is maintained.

6. A method for delivering a pumping fluid as set forth in claim 5, wherein, said specific amount is defined as a window size.

7. A method for delivering a pumping fluid as set forth in claim 5, wherein the specific amount is 0.1 ml.

8. A multiple cylinder pumping apparatus for delivering a liquid or supercritical fluid at a desired pumping pressure and mass flow rate with minimal fluctuations, comprising:
   a plurality of cylinders and associated pistons;
   sensing means for sensing pump parameters;
   means for calculating the compression displacement required to compensate for fluid compressibility, prior to the end of the pumping cycle, as a function of said sensed parameters; wherein, said calculating means generates drive signals corresponding to calculated final piston displacement which will compensate for said fluid compressibility;
   drive means coupled to said pistons for actuating said pistons in accordance to said drive signals to deliver said liquid or supercritical fluid at a desired pumping pressure and mass flow rate.

9. The apparatus of claim 8, wherein one of said sensed pump parameters is the pressure of the fluid at the output of the pump, and wherein, pressure measurements which are lower than expected indicate a leak in a particular pump cylinder, and wherein, said controller generates drives signals to increase the speed within the pump cycle, of said particular pump cylinder to compensate for said leaks.

10. The apparatus of claim 8, wherein said sensed pump parameters are the type of fluid being pumped, the initial piston displacement and initial pressure of the fluid within said cylinder.

11. The apparatus of claim 10, wherein said calculating means calculates the final temperature of the pumping fluid and the density of the pumping fluid at the final piston displacement as a function of said sensed parameters; and wherein, said calculating means calculates a pump speed which will maintain constant mass flow output regardless of the varying density.

12. The pumping apparatus as claimed in claim 10, wherein said sensed parameters further include the post-compression fluid temperature as a function of time.

* * * * *